(12) United States Patent
Cigada et al.

(10) Patent No.: US 7,740,481 B2
(45) Date of Patent: Jun. 22, 2010

(54) OSTEOINTEGRATIVE INTERFACE FOR IMPLANTABLE PROSTHESES AND A METHOD FOR THE TREATMENT OF THE OSTEOINTEGRATIVE INTERFACE

(75) Inventors: Alberto Cigada, Milan (IT); Roberto Chiesa, Vedano Olona (IT); Enrico Sandrini, Brescia (IT); Gianni Rondelli, Milan (IT); Matteo Santin, Brighton (GB)

(73) Assignee: Politecnico di Milano, Milan (IT)

( * ) Notice: Subject to any disclaimer, the term of this patent is extended or adjusted under 35 U.S.C. 154(b) by 1352 days.

(21) Appl. No.: 11/015,882

(22) Filed: Dec. 17, 2004

(65) Prior Publication Data

US 2005/0143743 A1    Jun. 30, 2005

(51) Int. Cl.
*A61C 8/00*    (2006.01)
(52) U.S. Cl. .................................. 433/201.1; 433/173
(58) Field of Classification Search ......... 433/172–176, 433/201.1; 623/23, 23.51, 23.55; 606/76; 427/2.26, 2.29; 205/318, 322
See application file for complete search history.

(56) References Cited

U.S. PATENT DOCUMENTS

| 4,801,300 | A | * | 1/1989 | Kurze et al. ............... 623/23.36 |
| 5,385,662 | A |   | 1/1995 | Kurze et al. |
| 5,478,237 | A |   | 12/1995 | Ishizawa |
| 5,723,038 | A | * | 3/1998 | Scharnweber et al. ....... 205/107 |
| 6,730,129 | B1 | * | 5/2004 | Hall ......................... 623/23.57 |
| 2004/0149586 | A1 | * | 8/2004 | Sul ............................ 205/171 |

FOREIGN PATENT DOCUMENTS

WO    PCT/SE02/0124    5/2002

OTHER PUBLICATIONS

"Ceramic-metal and ceramic-polymer composites prepared by a biomimetic process", Kokubo et al. Composites Part A: Applied Science and Manufacturing, Elzevier Science Publishers B.V. vol. 30, No. 4 Apr. 1999.
International Search Report of PCT/EP 03/05686.

* cited by examiner

*Primary Examiner*—Cris L Rodriguez
*Assistant Examiner*—Sunil K Singh
(74) *Attorney, Agent, or Firm*—Notaro, Michalos & Zaccaria P.C.

(57) ABSTRACT

An interface including a substrate of biocompatible material such as titanium, tantalum or their alloys having, on the surface of the substrate, a first layer having a first concentration of oxide of the biocompatible material, enriched with a second concentration of phosphorus and with a third concentration of calcium, the ratio between the concentration of calcium and the concentration of phosphorus being greater than two. The interface also includes a second layer having a first surface in contact with the first layer and a second surface. The second layer has a fourth concentration of oxide enriched with a fifth concentration of calcium and a sixth concentration of phosphorus. The fourth concentration is less than the fifth and sixth concentrations and the ratio between the fifth concentration of calcium and the sixth concentration of phosphorus is no less than three.

5 Claims, 1 Drawing Sheet

OSTEOINTEGRATIVE INTERFACE FOR IMPLANTABLE PROSTHESES AND A METHOD FOR THE TREATMENT OF THE OSTEOINTEGRATIVE INTERFACE

The present invention relates to an osteointegrative interface for implantable prostheses and to a method for the treatment of the osteointegrative interface, particularly to a biomimetic osteointegrative interface and to a method for modifying the surface of the osteointegrative interface superficially.

Biomimetic processes which simulate biomineralization processes have been used with success for preparing materials such as iron oxides, apatite, and cadmium sulphide which are used in various technological fields.

The field which has drawn most "inspiration" from biomineralization processes is the field of biomaterials and, in particular, biomaterials for orthopaedics, maxillo-facial surgery, and dentistry.

These materials have to interact with body tissues and should therefore possess particular biocompatibility and bioactivity qualities and mechanical properties.

The main uses of biomaterials in the hard tissues field include prostheses such as hip prostheses, knee prostheses, dental implants, screws, nails, plates and osteosynthesis means.

Because of the mechanical properties required, the materials usually used for prostheses are stainless steel, titanium, titanium alloys, and tantalum, which have the best biocompatibility characteristics of all of the metals.

These metals exhibit a high mechanical breaking load but require long implantation periods in order for their integration with the biological tissues such as, for example, bone, to be established.

To prevent this problem, there are known biomimetic treatments for osteointegrative interfaces, by means of which it is possible to bring about a significant increase in the rate of precipitation of hydroxyapatite after immersion in biological fluids, and its adhesion to the prosthesis.

Calcium phosphates, including hydroxyapatite, are the main constituents of the inert bone matrix.

U.S. Pat. No. 5,152,993 (Lars Magnus et al.) and U.S. Pat. No. 5,885,612 (Ohthuke et al.) propose a treatment in hydrogen peroxide with the use of hydrogen peroxide or hydrogen peroxide and metal ions, which modifies the surface of the prosthesis, promoting the formation of —OH hydroxyl functional groups which can induce the formation of a stable interface with bone.

U.S. Pat. No. 5,609,633 (Kokubo) and the corresponding application EP 678300A1 (Kokubo) teach a treatment based on immersion in an alkaline solution such as NaOH, KOH or $CaOH_2$, followed by washing and high-temperature heat treatment.

In particular, these two documents describe a treatment for etching with hydroxides an oxide such as titanium oxide, which is almost completely crystalline and is composed mainly of the rutile, anastase and, rarely, brookite phases, which are different crystalline forms of titanium dioxide, that is $TiO_2$.

This etching has the advantage not only of forming a larger number of —OH groups so that the surface layer hydroxylates more easily and is particularly significantly enriched with oxygen, but also of achieving the formation of a layer of amorphous calcium phosphates which are stoichiometrically similar to hydroxyapatite and can therefore promote the formation of mature hydroxyapatite.

The heat treatment included in this treatment with alkalis would lead to an increase of up to about 1 μm in the thickness of the titanium oxide layer.

To achieve a significant increase in the thickness of oxide which forms on the surface of a metal, anodic passivation treatments have been optimized by the development of a technique known as anodic spark deposition (ASD).

The ASD technique is a galvanic electrodeposition process which is performed at fairly high voltage and which causes point breakdown and perforation of the dielectric surface oxide layer which is formed progressively, thus allowing it to grow.

With this technique, as described, for example, in U.S. Pat. No. 5,385,662 (Kurze et al.), it is possible to produce coatings with the characteristics of sintered ceramic materials, which are particularly resistant to abrasion and corrosion, and with thicknesses of up to 150 μm.

With specific reference to bone implants, U.S. Pat. No. 5,478,237 (Ishizawa) teaches the use of this technique to bring about a modification of the composition, of the thickness, and of the morphology of the titanium oxide film, that is, the formation of a thick and nanoporous oxide film containing calcium and phosphorus, of a thickness clearly greater than that which is formed by natural oxidation of the metal.

However, this technique does not substantially improve the biomimetic properties of the titanium.

In order to improve its biomimetic capacity, the film or layer is subjected to a hydrothermic treatment which can promote nucleation of hydroxyapatite crystals. However, these crystals are not distributed homogeneously and do not cover the surface of the osteointegrative interface completely.

Homogeneity of behaviour is therefore not achieved.

Moreover, the mechanical bond between oxide and crystals is very weak.

In view of the prior art described, the object of the present invention is to modify superficially the surface of titanium, of tantalum, and of their alloys so as to produce biomimetic surfaces having structural and morphological characteristics that are innovative in comparison with those known from the prior art.

By virtue of the present invention, it is possible to achieve an increase in the thickness of the oxide film of titanium, of tantalum, or of their alloys from a few nanometres to a few micrometres by reducing, amongst other things, the extent to which metal ions are released from the implant. The adhesion of the oxide layer to the substrate is excellent.

The present invention, also enables elements such as calcium and phosphorus which can promote mineralization processes of the extxacellular bone matrix to be incorporated in the oxide film of titanium, of tantalum, or of their alloys.

Moreover, by virtue of the present invention it is possible to bring about, for example, in a sponge, the formation of nanometric porosity which can geometrically promote protein adhesion and consequently the adhesion of osteoblast cells.

Finally, by virtue of the present invention, it is possible to bring about the creation, within the titanium oxide film, that is, in its porosity, of -OH bonds which can form chemical bonds both with calcium and phosphorus ions, further promoting the mineralization of the extracellular matrix, and with proteins, further promoting osteoblast adhesion.

The characteristics and the advantages of the present invention will become clear from the following detailed description of a practical embodiment thereof which is illustrated by way of non-limiting example in the appended drawing, in which:

One of the most important requirements in applications for osteointegrative interfaces is to synthesize a surface with crystals of dimensions comparable to those of biological apatite, so that an increase in the surface area of the crystals can improve the interactions at the interface with the bone tissue and increase the capability of the material thus to create a bond with the bone tissue.

Figure 1:
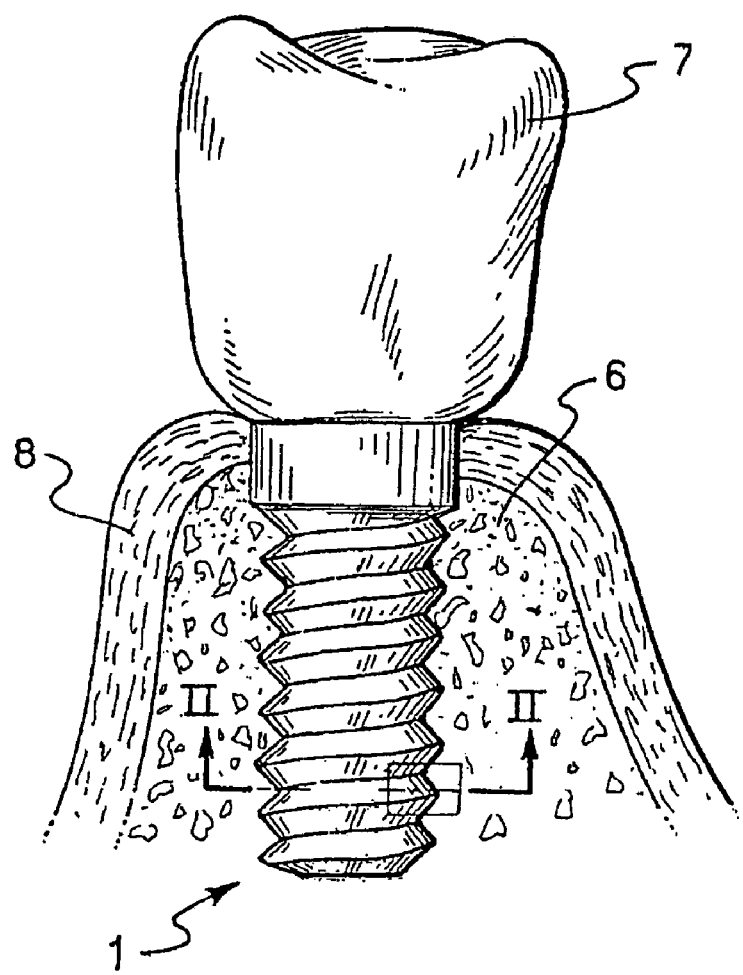
FIG. 1 shows, in section, an embodiment of an osteointegrative interface according to the present invention.
Figure 2:
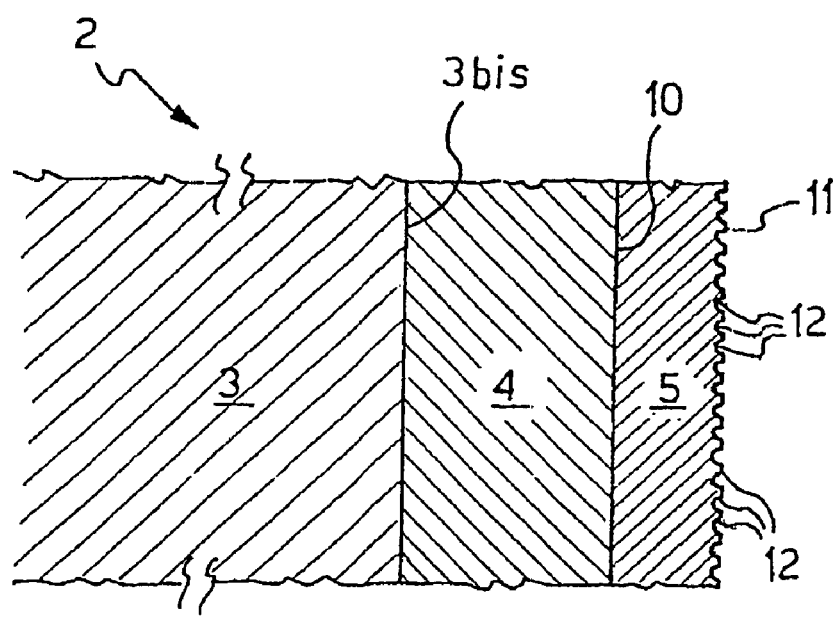
FIG. 2 is a section, taken on the line II-II, of the layers making up the surface of the osteointegrative interface of FIG. 1.

With reference to appended FIGS. 1 and 2, which show an example of an osteointegrative interface for a dental implant 1 according to the present invention, this requirement is satisfied.

With reference in particular to FIG. 2, an enlarged section through the implant 1, taken on the line II-II of FIG. 1 so as to show the layers making up the surface of the osteointegrative interface 1, is indicated 2.

These layers comprise a substrate 3 generically of titanium, a protective layer 4, generically of titanium oxide, superimposed on the surface 3bis of the substrate 3, and a surface layer 5 superimposed on the protective layer 4.

FIG. 1 shows the dental implant 1 which has, for example, the shape of a screw, and which has been inserted in a bone socket 6; a tooth crown is indicated 7 and the gum is indicated 8.

Naturally, the shape and size of the implant must be selected in dependence on the specific application and the example shown in FIG. 1 is only one of the possible embodiments.

In particular, the substrate 3 which constitutes the core of the dental implant 1 is composed of transition metals, for example, of titanium, of tantalum, or of their alloys.

If the substrate 3 is made of titanium, the protective layer 4 will comprise titanium oxide which is formed by the process described below to reach a thickness of the order of a few μm, for example 5-1.0 μm.

In the innovative embodiment, this protective layer 4 is enriched throughout its thickness of 5-1.0 μm with a relatively uniform and high concentration of elements such as calcium and phosphorus, the concentration of the element calcium being greater than the concentration of phosphorus, for example, more than 2 times greater, that is Ca/P>2.

The surface layer 5, which has a thickness of the order of tens of nanometres and is superimposed on the protective layer 4, comprises the same elements as the protective layer 4 but these elements have concentration ratios between calcium and titanium, that is Ca/Ti, and between phosphorus and titanium, that is P/Ti, which tend to be greatly in favour of the elements which constitute the enrichment, that is (Ca+P)/Ti>80%. Moreover the Ca/P ratio is higher and is equal to about Ca/P≅3 or even more.

Moreover, it can be seen that the surface layer 5 has a lower surface 10 and an upper surface 11, the lower surface 10 being in contact with the titanium oxide layer 4 and the upper surface 11 being in contact with the bone socket 6.

The layer 5, particularly on the upper surface 11, is also characterized by the presence of a high concentration of —OH chemical coupling groups, suitable for forming a plurality of nucleation centres 12.

The osteointegrative interface thus described is produced by a series of steps which are described below.

In a first step, the surface 3bis of the implant 1 is subjected to a mechanical or even chemical finishing treatment with abrasive paper, sandblasting, or the like, to produce a surface with controlled and homogeneous roughness with Ra values of the order of 1-2 μm for dental implants and greater values for non-cemented orthopaedic prostheses.

There is then a second step of cleaning of the upper surface 3bis with the use, for this purpose, of an ultrasound chamber containing acetone for a first period of time included within a time interval where 3<t<5 minutes and distilled water for a second period of time, where 3<t<5 minutes.

This step is useful since it enables dirt particles and/or impurities to be removed from the surface 3bis of the substrate 3.

A third step is then provided for; in this step a first anodic spark deposition (ASD) treatment takes place in an aqueous calcium glycerophosphate (Ca-GP) solution at a concentration of 0.015 M with a maximum variation of about ±0.005M. This step provides for treatment at about T=0° C., preferably with a maximum variation of ±1° C. and with a predetermined current-intensity value of about 70 A/M$^2$, whilst the potential rises freely to a predetermined final value of about 350 V. This brings about the growth of the protective layer 4 and the deposition therein of a predetermined quantity of phosphorus and also some calcium.

The mechanical adhesion of the protective layer to the substrate is outstanding.

The third step ends when the potential reaches 350 V and the current intensity is still about 70 A/M$^2$.

A fourth step is then performed in which washing in distilled water and careful drying of the osteointegrative implant 1 thus treated take place.

The fifth step provides for a second ASD treatment in an aqueous solution of calcium hydroxide [Ca(OH)$_2$] at a concentration of 0.1 M with a maximum variation of ±0.02M. For a first period of time, the treatment is performed at a temperature of between two and eight degrees centigrade, that is 2° C.<T<8° C., with a constant current intensity of about 70 A/m$^2$ whilst the potential is allowed to rise to a final value of about 370 V.

The fifth step continues for a second period of time with deposition at a constant voltage of about 370 V and simultaneous reduction in current to a predetermined value of about 35 A/M$^2$.

The layer 4 is thus modified and incorporates further calcium.

It should be noted that the final current intensity is equal to half of the initial current used during the first stage of the second ASD treatment.

There is then a sixth step which provides for further washing in distilled water and careful drying of the implant 1 thus treated.

The seventh step provides for the immersion of the osteointegrative implant 1 thus treated in 5 M aqueous KOH solution (or even NaOH, but with less satisfactory results) kept at T=60° C. for t=24 h.

Finally, an eighth step is provided for; in this step a final washing in distilled water and careful drying of the interface thus treated take place.

In particular, it should be noted that the third step, that is the first ASD, produces a titanium oxide layer 4 which is rich in phosphorus and partially in calcium so as to give rise to a dielectric with a thickness of the order of a few μm (possibly about ten μm) which permits the application of the high voltages that are required in the second ASD.

In fact, without a first deposition and thickening of the surface oxide, it is impossible to bring the osteointegrative implant 1 to a voltage high enough to perform the second ASD treatment in Ca(OH)$_2$ solution, which is a solution without anions such as to be able to ensure the formation of an adequate dielectric thickness.

Basically, whereas with the first ASD a titanium oxide layer of the desired thickness, provided with a first concentration of calcium and phosphorus, is formed, with the second ASD treatment, the layer is thickened and there is an increase in the Ca/P ratio.

Moreover, the second ASD treatment is preparatory to the formation of nucleation centres characterized by the presence of surface —OH chemical groups.

The seventh step, that is, the immersion of the interface 1 in a KOH solution, further increases the Ca/P ratio, since phosphorus is extracted from the surface portion of the layer 4 so as to favour its hydration and a high concentration of —OH groups is produced on the surface.

The fifth step and the seventh step thus produce a surface layer 5 in which the Ca/Ti and P/Ti ratios tend to be greatly in favour of the two elements which constitute the enrichment, to the extent that the surface layer 5 is composed, in its last nanometres, substantially by calcium and phosphorus, with a Ca/P ratio close to four and in any case no less than three.

Moreover, by virtue of the innovative treatment method, the surface layer 5 is rich in —OH chemical coupling groups which favour the deposition of calcium and phosphorus in a physiological solution.

Although, in the description, reference is made specifically to titanium osteointegrative interfaces, clearly the invention put forward is also applicable to interfaces made of tantalum and of alloys of titanium and of tantalum.

The invention claimed is:

1. A biomimetic osteointegrative interface comprising:
   a substrate (3) of biocompatible material selected from the group consisting of: titanium, tantalum, and alloys thereof, the substrate having a surface (3*bis*);
   the interface comprising, on the surface (3*bis*) of the substrate (3), a first layer (4) having a first concentration of oxide of the biocompatible material, selected from the group consisting of: titanium oxide, tantalum oxide and oxide of alloys of said titanium, enriched with a second concentration of phosphorus and with a third concentration of calcium, the ratio between the concentration of calcium and the concentration of phosphorus being greater than two;
   the biomimetic osteointegrative interface further comprising:
   a second layer (5) having a first surface (10) in contact with the first layer (4), and a second surface (11), the second layer (5) having a fourth concentration of oxide enriched with the same oxide present in the first layer (4) and with a fifth concentration of calcium and a sixth concentration of phosphorus, the fourth concentration being less than the fifth and the sixth concentrations and the ratio between the fifth concentration of calcium and the sixth concentration of phosphorus being no less than three.

2. The biomimetic osteointegrative interface according to claim 1, wherein the second layer (5) has a gradient of the fifth calcium concentration and of the sixth phosphorus concentration which gradient increases from the first surface (10) towards the second surface (11) of the second layer (5).

3. A biomimetic osteointegrative interface according to claim 1, wherein the second layer (5) is hydrated and has —OH hydroxyl chemical coupling groups suitable for forming a plurality of nucleation centers (12).

4. A biomimetic osteointegrative interface comprising:
   a substrate (3) of biocompatible material selected from the group consisting of: titanium, tantalum, and alloys thereof, the substrate having a surface (3*bis*);
   the interface comprising, on the surface (3*bis*) of the substrate (3), a first layer (4) having a first concentration of oxide of the biocompatible material, selected from the group consisting of: titanium oxide, tantalum oxide and oxide of alloys of said titanium and tantalum that is enriched with a second concentration of phosphorus and with a third concentration of calcium, the ratio between the concentration of calcium and the concentration of phosphorus being greater than two;
   the biomimetic osteointegrative interface (1) further comprising:
   a second layer (5) having a first surface (10) in contact with the first layer (4), and a second surface (11), the second layer (5) having a fourth concentration of oxide that is the same oxide present in the first layer and enriched with a fifth concentration of calcium and a sixth concentration of phosphorus, the fourth concentration being less than the fifth and the sixth concentrations and the ratio between the fifth concentration of calcium and the sixth concentration of phosphorus being no less than three; and
   wherein the second layer (5) is hydrated and has —OH hydroxyl chemical coupling groups suitable for forming a plurality of nucleation centers (12).

5. The biomimetic osteointegrative interface according to claim 4, wherein the second layer (5) has a gradient of the fifth calcium concentration and of the sixth phosphorus concentration which gradient increases from the first surface (10) towards the second surface (11) of the second layer (5).

* * * * *

UNITED STATES PATENT AND TRADEMARK OFFICE
CERTIFICATE OF CORRECTION

PATENT NO. : 7,740,481 B2
APPLICATION NO. : 11/015882
DATED : June 22, 2010
INVENTOR(S) : Alberto Cigada et al.

Page 1 of 1

It is certified that error appears in the above-identified patent and that said Letters Patent is hereby corrected as shown below:

On the cover page, please add the following fields as follows (63) and (30):

Related U.S. Application Data

(63) Continuation of application No. PCT/EP03/05686, filed May 30, 2003.

(30) Foreign Application Priority Data

June 21, 2002 (IT) MI2002A001377

Signed and Sealed this

Second Day of November, 2010

David J. Kappos
*Director of the United States Patent and Trademark Office*